United States Patent
Ortashi et al.

(10) Patent No.: US 10,588,929 B1
(45) Date of Patent: Mar. 17, 2020

(54) METHOD OF SYNTHESIZING WATERMELON SEED PARTICLES

(71) Applicant: KING SAUD UNIVERSITY, Riyadh (SA)

(72) Inventors: Khalid Mustafa Osman Ortashi, Riyadh (SA); Manal Ahmed Gasmelseed Awad, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/428,515

(22) Filed: May 31, 2019

(51) Int. Cl.
| | | |
|---|---|---|
| *A61K 36/42* | (2006.01) | |
| *A61P 31/04* | (2006.01) | |
| *A61K 9/51* | (2006.01) | |
| *B82Y 5/00* | (2011.01) | |

(52) U.S. Cl.
CPC ............ *A61K 36/42* (2013.01); *A61K 9/5192* (2013.01); *A61P 31/04* (2018.01); *B82Y 5/00* (2013.01)

(58) Field of Classification Search
None
See application file for complete search history.

(56) References Cited

U.S. PATENT DOCUMENTS 9,789,146 B1 * 10/2017 Awad .................. A61K 36/185

FOREIGN PATENT DOCUMENTS

| CN | 103462100 A | 12/2013 |
|---|---|---|
| CN | 103651893 A | 3/2014 |

OTHER PUBLICATIONS

Jarret R. et al. Oil and Fatty Acid Contents in Seed of *Citrullus lanatus* Schrad. J Agricultural Food Chemistry 60:5199-5204, Apr. 2012. (Year: 2012).*
Adelani-Akande T. et al. Antibacterial Activity of Watermelon (*Cirullus lanatus*) Seed Against Selected Microorganisms. African J of Biotechnology 14(14)1224-1229, Apr. 2015. (Year: 2015).*
Muller, R. and Peters, K., "Nanosuspensions for the formulation of poorly soluble drugs: I. Preparation by a size-reduction technique," Inter'l J. of Pharmaceutics, 160(2): pp. 229-237, 1998.
Milovanovic, M. and Picuric-Jovanovic, K., "Characteristics and Composition of Melon Seed Oil," J. of Ag. Sci. 50(1): pp. 41-47, 2005.
Oseni, O.A. and Okoye, V.I., "Studies of Phytochemical and Antioxidant properties of the Fruit of Watermelon (*Citrillus lanaturs*), (Thunb.)," J. Pharm Biomed Sci. 27(27): pp. 508-514, 2013.
Dash, P. and Ghosh, G., "Fractionation, amino acid profiles, antimicrobial and free radical scavenging activities of *Citrullus lanatus* seed protein," Natural Products Research, 2017.
Bhawana et al., "Curcumin Nanoparticles: Preparation, Characterization, and Antimicrobial Study," J. of Agricultural and Food Chemistry 59: pp. 2056-2061, 2011.

* cited by examiner

*Primary Examiner* — Ralph J Gitomer
(74) *Attorney, Agent, or Firm* — Richard C. Litman; Nath, Goldberg & Meyer

(57) ABSTRACT

The watermelon seed nanoparticles may be synthesized by dissolving powdered watermelon seeds in a solvent to produce a first mixture, adding the first mixture dropwise to boiling water under ultrasonic conditions to produce a second mixture, sonicating the second mixture and drying the second mixture to produce watermelon seed nanoparticles. In an embodiment, the watermelon seeds may be *Citrullus lanatus* seeds. In an embodiment, the watermelon seed nanoparticles may be included in a pharmaceutical composition, such as an antimicrobial or anti-cancer composition.

8 Claims, 3 Drawing Sheets

METHOD OF SYNTHESIZING WATERMELON SEED PARTICLES

BACKGROUND

1. Field

The disclosure of the present patent application relates to nanotechnology, and particularly to a method of producing watermelon seed nanoparticles and their use in pharmaceutical compositions.

2. Description of the Related Art

In materials science, nanomaterials have demonstrated unique size and morphology based characteristics. Nanotechnology is an emerging field demonstrating significant potential for the development of new medicines. Nanomaterials have demonstrated improved oral bioavailability and solubility. The most common methods of producing nanoparticles are chemical or mechanical, including ball milling, thermal quenching, precipitation techniques, and vapor deposition. However, these methods are often costly, and may result in toxic byproducts.

Biological approaches for synthesizing nanoparticles can avoid many of the disadvantages associated with the chemical or mechanical synthesis methods.

Thus, watermelon seed nanoparticles are desired.

SUMMARY

The watermelon seed nanoparticles may be synthesized by dissolving powdered watermelon seeds in a solvent to produce a first mixture, adding the first mixture dropwise to boiling water under ultrasonic conditions to produce a second mixture, sonicating the second mixture and drying the second mixture to produce watermelon seed nanoparticles.

An embodiment of the present subject matter is directed to watermelon seed nanoparticles.

An embodiment of the present subject matter is directed to a pharmaceutical composition comprising the watermelon seed nanoparticles and a pharmaceutically acceptable carrier.

An embodiment of the present subject matter is directed to a method of making a pharmaceutical composition including mixing the watermelon seed nanoparticles with a pharmaceutically acceptable carrier.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
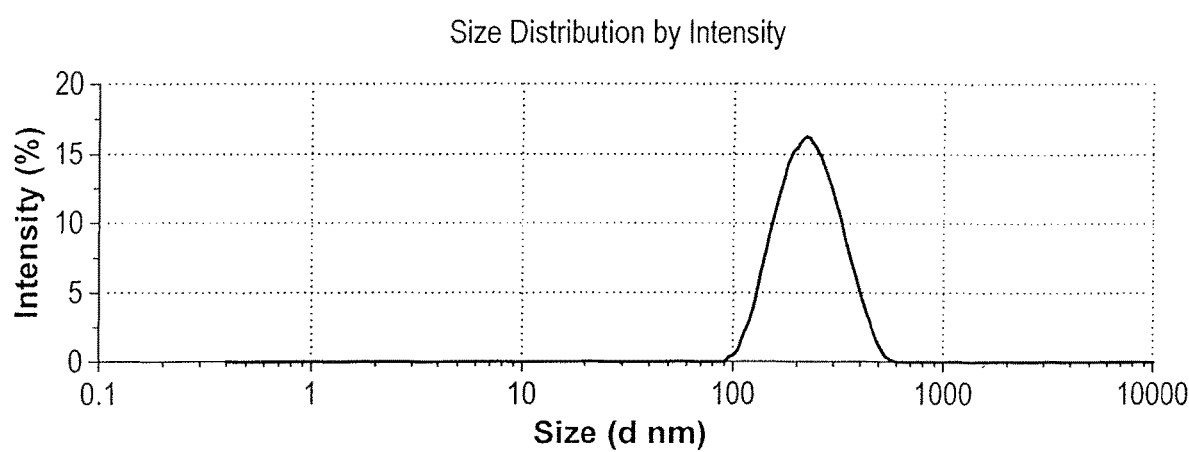
FIG. 1 depicts a zeta sizer spectrum of the watermelon seed nanoparticles.

The watermelon seed nanoparticles may be synthesized by dissolving powdered watermelon seeds in a solvent to produce a first mixture, adding the first mixture dropwise to boiling water under ultrasonic conditions to produce a second mixture, sonicating the second mixture and drying the second mixture to produce watermelon seed nanoparticles.

In an embodiment, the powdered watermelon seeds may be synthesized by obtaining *Citrullus lanatus* seeds, washing the seeds with distilled water, drying the seeds, grinding the dried seeds and separating the watermelon seed powder using a sieve of 0.355 mm.

*Citrullus lanatus* is an herbaceous creeping watermelon plant originating from the Kalahari Desert of southern Africa. A single *Citrullus lanatus* plant may produce an average of 3 to 5 fruits weighing 3 to 8 kg each. The watermelon seeds of the *Citrullus lanatus* are a potential source of many desirable trace components, including but not limited to zinc, magnesium, calcium, protein, B vitamins, fats, and other minerals.

In an embodiment, the solvent may be methanol.

As used herein, the term "about," when used to modify a numerical value, means within ten percent of that numerical value.

An embodiment of the present subject matter is directed to watermelon seed nanoparticles. The watermelon seed nanoparticles may have an average diameter of 215 nm. The watermelon seed nanoparticles may be spherical and well dispersed. The watermelon seed nanoparticles may have antimicrobial activity, including but not limited to antifungal activity, anti-gram-positive bacterial activity, and anti-gram-negative bacterial activity. The watermelon seed nanoparticles may also have anti-cancer activity. In an embodiment, the watermelon seed nanoparticles may kill cancer cells, including but not limited to colon cancer cells or breast cancer cells.

An embodiment of the present subject matter is directed to a pharmaceutical composition comprising the watermelon seed nanoparticles and a pharmaceutically acceptable carrier.

An embodiment of the present subject matter is directed to a method of making a pharmaceutical composition including mixing the watermelon seed nanoparticles with a pharmaceutically acceptable carrier. For example, the method of making a pharmaceutical composition can include mixing the watermelon seed nanoparticles under sterile conditions with a pharmaceutically acceptable carrier with preservatives, buffers, and/or propellants to create the pharmaceutical composition.

An embodiment of the present subject matter is directed to a pharmaceutical composition including the watermelon seed nanoparticles. To prepare the pharmaceutical composition, the watermelon seed nanoparticles, as the active ingredient, are intimately admixed with a pharmaceutically acceptable carrier according to conventional pharmaceutical compounding techniques. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents, and the like. Further, for solid oral preparations, suitable carriers and additives include starches, sugars, diluents, granulating agents, lubricants, binders, disintegrating agents, and the like.

The present compositions can be in unit dosage forms such as tablets, pills, capsules, powders, granules, ointments, sterile parenteral solutions or suspensions, metered aerosol or liquid sprays, drops, ampules, auto-injector devices or suppositories, for oral parenteral, intranasal, sublingual or rectal administration, or for administration by inhalation or insufflation. The active compound can be mixed under sterile conditions with a pharmaceutically acceptable carrier and, if required, any needed preservatives, buffers, or propellants. The composition can be presented in a form suitable for daily, weekly, or monthly administration. The pharmaceutical compositions herein will contain, per dosage unit, e.g., tablet, capsule, powder, injection, teaspoonful, suppository and the like, an amount of the active ingredient necessary to deliver an effective dose.

The following examples illustrate the present teachings.

Example 1

Synthesis of Watermelon Seed Nanoparticles

Watermelon seed nanoparticles were synthesized as follows. Watermelon seeds of *Citrullus lanatus* were obtained from a market in Riyadh, Saudi Arabia. The watermelon seeds were washing with distilled water and dried. The dried watermelon seeds were ground to produce watermelon seed powder, and the watermelon seed powder was filtered through a sieve of 0.355 mm and stored for later use. About 500 mg of the watermelon seed powder was then dissolved in 10 ml methanol to form a first mixture. The first solution was then added dropwise to 40 ml of boiling water, under ultrasonic conditions at a flow rate of about 0.1-0.3 ml/min over 10 minutes, to form a second mixture. The second mixture was sonicated for 20 minutes, stirred for a further 15 minutes, and dried, producing the watermelon seed nanoparticles.

Example 2

Characterization of Watermelon Seed Nanoparticles

Figure 2A:
FIG. 2A depicts a transmission electron micrograph of the watermelon seed nanoparticles.
Figure 2B:
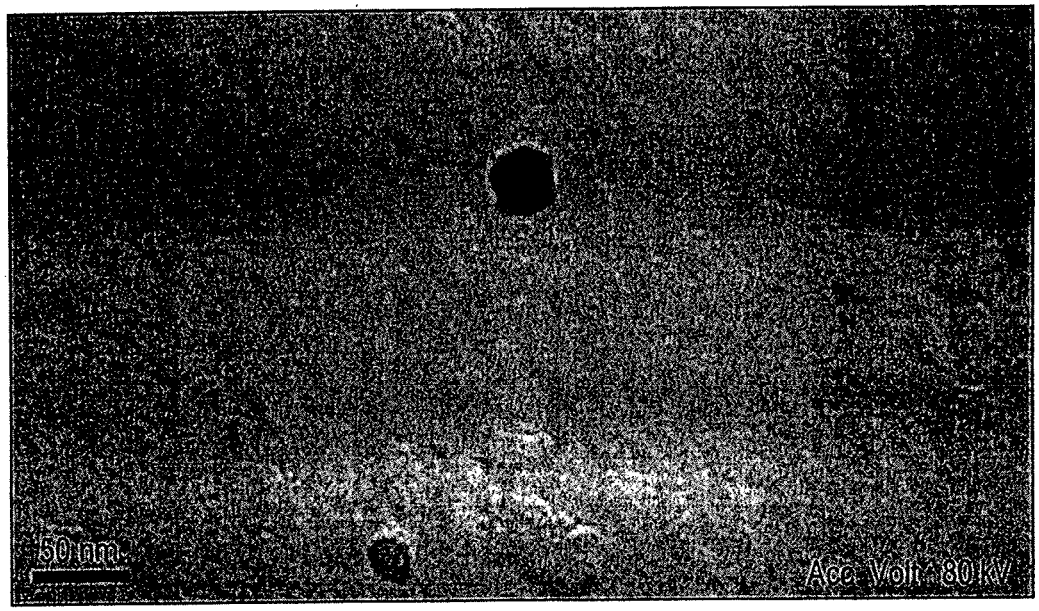
FIG. 2B depicts a transmission electron micrograph of the watermelon seed nanoparticles.

Watermelon seed nanoparticles synthesized according to Example 1 were characterized as follows. The watermelon seed nanoparticles were analyzed in a zeta-sizer, revealing an average diameter of 215 nm and a polydispersity index of 0.111, indicating that the nanoparticles are colloidal, display long term stability, and have a high dispersity. (See FIG. 1 and Table 1) Transmission electron micrographs demonstrated that the watermelon seed nanoparticles are spherical to round in shape and well dispersed, without agglomeration (See FIGS. 2A-2B)

TABLE 1

Zeta-sizer characterization of watermelon seed nanoparticles

|  |  |  | Size (d.nm) | % Intensity | St Dev (d.nm) |
|---|---|---|---|---|---|
| Z-avg (d.nm) | 215.0 | | | | |
| PdI | 0.111 | Peak 1 | 238.2 | 100.0 | 80.15 |
| Intercept | 0.942 | Peak 2 | 0.000 | 0.0 | 0.000 |
| Quality | Good | Peak 3 | 0.000 | 0.0 | 0.000 |

Example 3

Antimicrobial Activity of the Watermelon Seed Nanoparticles

Watermelon seed nanoparticles synthesized according to Example 1 were tested for antimicrobial activity against gram negative bacteria, gram positive bacteria, and fungi. Zone of inhibition studies were performed, the results of which are summarized in Table 2 (displaying mean zone of inhibition in mm ± standard deviation beyond well diameter of 6 mm). Testing used the diffusion agar technique with 6.0 mm well diameter and administration of 100 μg of the watermelon seed nanoparticles.

TABLE 2

Antimicrobial Activity of the Watermelon Seed Nanoparticles

| Micro-organism | Nanoparticles | Control |
|---|---|---|
| FUNGI | | Amphotericin B |
| *Aspergillus fumigatus* (RCMB 02567) | 20.7 ± 1.5 | 21.7 ± 1.5 |
| Gram Positive Bacteria | | Ampicillin |
| *Streptococcus pneumoniae* (RCMB 010011) | 16.7 ± 1.5 | 21.0 ± 1.0 |
| *Bacillus subtilis* (RCMB 010068) | 22.7 ± 1.5 | 31.3 ± 1.5 |
| Gram Negative Bacteria | | Gentamicin |
| *Escherichia coli* (RCMB 010054) | 22.0 ± 1.0 | 20.3 ± 0.58 |

Example 4

Cytotoxic Activity of the Watermelon Seed Nanoparticles Against Cancerous Cells

Figure 3:
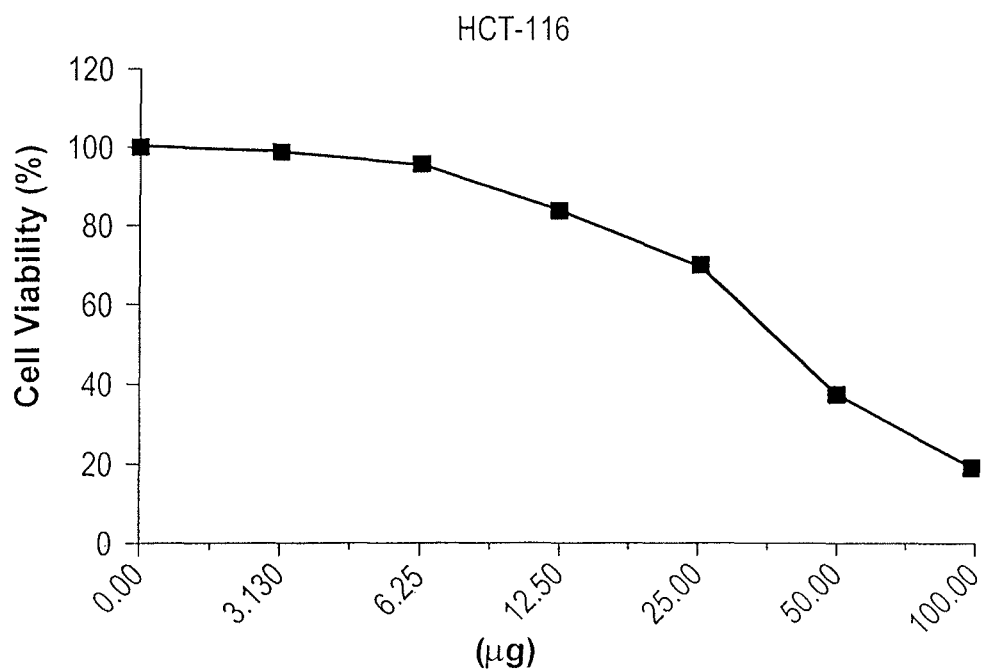
FIG. 3 depicts a graph of the cytotoxic effect of the watermelon seed nanoparticles on HCT-116 cells.
Figure 4:
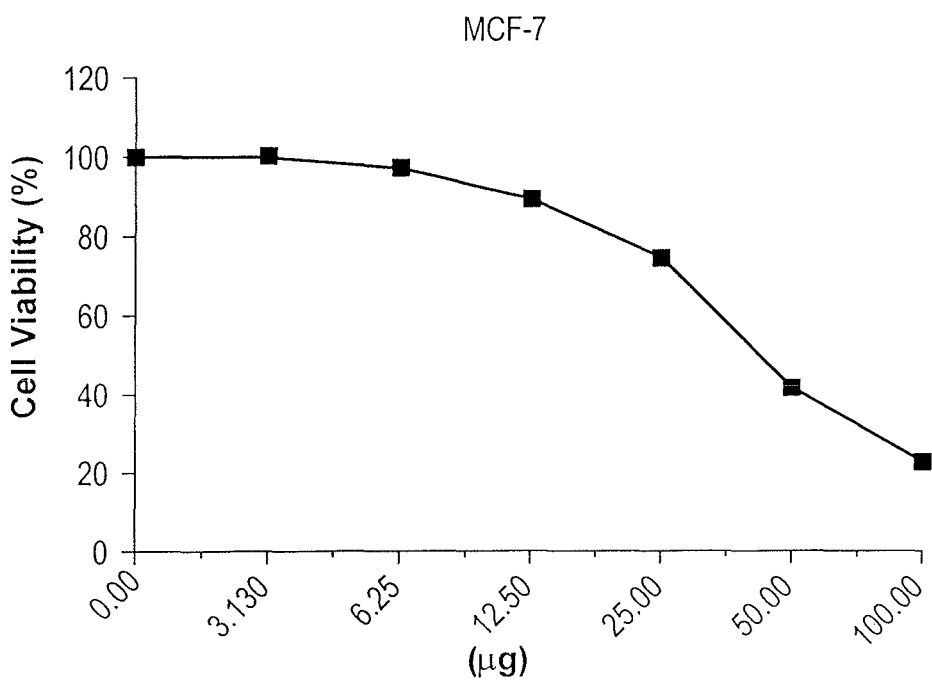
FIG. 4 depicts a graph of the cytotoxic effect of the watermelon seed nanoparticles on MCF-7 cells.

Watermelon seed nanoparticles synthesized according to Example 1 were tested for cytotoxicity against colon cancer cells (FICT-116) and breast cancer cells (MCF-7). The results of these tests are presented in Tables 3-4 and FIGS. 3-4. The watermelon seed nanoparticles displayed inhibitory activity against HCT-116 cells with an $IC_{50}$ of 40.1 μg. The watermelon seed nanoparticles also displayed inhibitory activity against MCF-7 cells with an $IC_{50}$ of 4.36 μg.

TABLE 3

Cytotoxic Activity of Watermelon Seed Nanoparticles Against HCT-116 Cells.

| Conc. | Viability % (Replicates) | | | | Inhibition | Std. Dev. |
|---|---|---|---|---|---|---|
| (μg) | 1st | 2nd | 3rd | Mean | % | (±) |
| 100 | 17.94 | 18.25 | 21.39 | 19.19 | 80.81 | 1.91 |
| 50 | 39.72 | 36.88 | 35.16 | 37.25 | 62.75 | 2.30 |
| 25 | 72.34 | 67.52 | 68.47 | 69.44 | 30.56 | 2.55 |
| 12.5 | 81.63 | 85.91 | 82.65 | 83.40 | 16.60 | 2.24 |
| 6.25 | 95.16 | 97.62 | 94.28 | 95.69 | 4.31 | 1.73 |
| 3.125 | 98.73 | 100 | 97.63 | 98.79 | 1.21 | 1.19 |
| 0 | 100 | 100 | 100 | 100 | 0.00 | |

TABLE 4

Cytotoxic Activity of Watermelon Seed Nanoparticles Against MCF-7 Cells.

| Conc. | Viability % (Replicates) | | | | Inhibition | Std. Dev. |
|---|---|---|---|---|---|---|
| (μg) | 1st | 2nd | 3rd | Mean | % | (±) |
| 100 | 21.87 | 19.93 | 24.51 | 22.10 | 77.90 | 2.30 |
| 50 | 39.56 | 43.87 | 40.92 | 41.45 | 58.55 | 2.20 |
| 25 | 74.18 | 70.63 | 79.14 | 74.65 | 25.35 | 4.27 |
| 12.5 | 89.65 | 87.18 | 91.78 | 89.54 | 10.46 | 2.30 |
| 6.25 | 97.52 | 96.64 | 98.16 | 97.44 | 2.56 | 0.76 |
| 3.125 | 100 | 99.71 | 100 | 99.90 | 0.10 | 0.17 |
| 0 | 100 | 100 | 100 | 100 | 0.00 | |

It is to be understood that the watermelon seed nanoparticles are not limited to the specific embodiments described above, but encompass any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing watermelon seed particles, comprising:
   (a) dissolving a watermelon seed powder in a solvent to produce a first mixture;
   (b) adding the first mixture dropwise to boiling water under ultrasonic conditions to produce a second mixture;
   (c) sonicating the second mixture; and
   (d) drying the second mixture to obtain watermelon seed particles.

2. The method of claim 1, further comprising: grinding *Citrullus lanatus* seeds to produce the watermelon seed powder.

3. The method of claim 1, wherein the solvent is methanol.

4. The method of claim 1, further comprising dissolving about 500 mg of the watermelon seed powder in 10 ml methanol to produce the first mixture.

5. The method of claim 1, further comprising adding the first mixture dropwise to 40 ml of boiling water, under ultrasonic conditions at a flow rate of about 0.1-0.3 ml/min over 10 minutes to produce the second mixture.

6. The method of claim 1, further comprising sonicating the second mixture for 20 minutes.

7. The method of claim 1, further comprising stirring the sonicated second mixture for 15 minutes.

8. The method of claim 1, wherein the watermelon seed particles have an average diameter of 215 nm.

* * * * *